United States Patent
Mattos et al.

(10) Patent No.: US 10,588,284 B2
(45) Date of Patent: Mar. 17, 2020

(54) HYBRID RICE HR170003

(71) Applicant: RICETEC, INC., Alvin, TX (US)

(72) Inventors: Luiz Mattos, Santa Maria (BR); Clauber Mateus Priebe Bervald, Santa Maria (BR)

(73) Assignee: RICETEC, INC., Alvin, TX (US)

( * ) Notice: Subject to any disclaimer, the term of this patent is extended or adjusted under 35 U.S.C. 154(b) by 0 days.

(21) Appl. No.: 16/058,743

(22) Filed: Aug. 8, 2018

(65) Prior Publication Data

US 2019/0059312 A1 Feb. 28, 2019

Related U.S. Application Data

(60) Provisional application No. 62/552,948, filed on Aug. 31, 2017.

(51) Int. Cl.
*A01H 5/10* (2018.01)
*A01H 6/46* (2018.01)

(52) U.S. Cl.
CPC ............ *A01H 6/4636* (2018.05); *A01H 5/10* (2013.01)

(58) Field of Classification Search
None
See application file for complete search history.

(56) References Cited

U.S. PATENT DOCUMENTS 7,005,567 B2 * 2/2006 Tillman .................. A01H 5/10
435/421

* cited by examiner

*Primary Examiner* — Medina A Ibrahim
(74) *Attorney, Agent, or Firm* — Barnes & Thornburg LLP; Alice O Martin

(57) ABSTRACT

Plants, seeds and tissue cultures of the hybrid rice HR170003, and methods for producing a rice plant by crossing a rice plant of hybrid rice HR170003 with itself or with another rice plant, such as a plant of another rice variety or rice hybrid, are disclosed.

18 Claims, No Drawings

HYBRID RICE HR170003

CROSS REFERENCE TO RELATED APPLICATIONS

The application claims the benefit of priority under 35 U.S.C. § 119(e) to U.S. Provisional Application No. 62/552,948, filed Aug. 31, 2017. The disclosure set forth in the referenced application is incorporated herein by reference in its entirety.

BACKGROUND

A new and distinctive hybrid rice designated HR170003 is disclosed.

Rice is an ancient agricultural crop and is today one of the principal food crops of the world. There are two cultivated species of rice: *Oryza sativa* L., the Asian rice, and *Oryza glaberrima* Steud, the African rice. The Asian species constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California. The Gulf Coast and Mississippi Delta regions mostly use a dry-seeded method of sowing rice whereas; California usually uses a water-seeded method.

Rice in the United States is classified into three primary market types by grain size and shape as: long-grain, medium-grain, and short-grain. Typical U. S. long-grain rice cooks dry and fluffy when steamed or boiled, whereas medium- and short-grain rice cooks moist and sticky. Long-grain cultivars have been traditionally grown in the Southern states.

Although specific breeding objectives vary somewhat in the different regions, increasing yield is a primary objective in all programs. Grain yield of rice is determined by the number of panicles per unit area, the number of fertile florets per panicle, and grain weight per fertile floret. Increases in any or all of these yield components provide a mechanism to obtain higher yields. Heritable variation exists for all of these components, and breeders may directly or indirectly select for increases in any of them.

The development of uniform hybrid rice requires developing homozygous inbred plants, crossing those inbred plants and evaluating those crosses. Pedigree selection, backcross selection, single seed selection, or combinations of these methods are used to develop inbred plants from breeding populations. Those breeding methods combine the genetic background from two or more inbred plants or various other sources of germplasm, such as, breeding pools from which new inbred plants are developed by selfing, combined with phenotypic or genotypic selection. The new inbred plants are crossed with other inbred plants and the hybrids created by those crosses are evaluated for commercial potential. Important commercial traits in hybrid rice may include higher yield, resistance to diseases and insects, herbicide tolerance, better stems and roots, tolerance to low temperatures, better agronomic characteristics, and grain quality.

Each breeding program usually includes a periodic, objective evaluation of the efficiency of the breeding procedure. Evaluation criteria vary depending on the goal and objectives, but may include gain from selection per year based on comparisons to an appropriate standard, overall value of the advanced breeding hybrids, and number of successful cultivars produced per unit of input (e.g., per year, per dollar expended, etc.). Promising advanced rice hybrids are thoroughly tested and compared to appropriate standards in environments representative of the commercial target area(s) for at least three or more years. The best hybrids are candidates for new commercial products. These processes, which lead to the final step of marketing and distribution, usually take from 8 to 12 years from the time the first cross is made to develop inbred parent lines to the subsequent development of improved hybrid rice. Therefore, development of new hybrid rice is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Each breeding cycle, the plant breeder selects the germplasm to advance to the next generation. This germplasm is grown under unique and different geographical, climatic and soil conditions and further selections are then made throughout the growing season. The inbred lines which are developed are unpredictable because the breeder's selection occurs in unique environments, with no control at the DNA level (using conventional breeding procedures), and with millions of different possible genetic combinations being generated. This unpredictability results in the expenditure of large amounts of research monies to develop superior new rice cultivars.

Testing is aimed at detecting any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar takes into consideration research and development costs as well as technical superiority of the final cultivar. For seed-propagated cultivars, it is desirable to produce seed easily and economically.

Rice, *Oryza sativa* L., is an important and valuable field crop. Thus, a continuing goal of rice breeders is to develop stable, high yielding rice cultivars that are agronomically sound. The reasons for this goal are to maximize the amount of grain produced on the land used and to supply food for both animals and humans. To accomplish this goal, the rice breeder must select and develop rice plants that have the traits that result in superior cultivars.

SUMMARY

Disclosed and described are hybrid rice seeds designated HR170003, wherein a representative sample of seed was deposited under ATCC Accession No. PTA-124255, a rice plant, or a part thereof, produced by growing the seed, and pollen or an ovule of the plant.

A tissue culture of cells produced from a plant designated HR170003, or a plant part selected from the group consisting of leaves, pollen, embryos, cotyledon, hypocotyl, meristematic cells, roots, root tips, pistils, anthers, flowers, stems, glumes and panicles, and a protoplast produced from the plant or tissue culture, are also within the scope of the disclosure.

A rice plant may be regenerated from the tissue culture, wherein the plant has essentially all of the morphological and physiological characteristics of hybrid rice HR170003, as listed in Table 1.

A method for producing a hybrid rice seed, includes crossing the HR170003 plant with a different rice plant and harvesting the resultant hybrid rice seed.

A method of producing a herbicide resistant rice plant, includes transforming the rice plant with a transgene, wherein the transgene confers tolerance to a herbicide selected from the group consisting of imidazolinone, cyclohexanedione, sulfonylurea, glyphosate, glufosinate, phenoxy proprionic acid, isoxazole, triketone, L-phosphinothricin, triazine and benzonitrile.

A method of producing an insect resistant rice plant, includes transforming the rice plant with a transgene that confers insect resistance.

A method of producing a rice plant with modified fatty acid metabolism or modified carbohydrate metabolism, include transforming the rice plant with a transgene encoding a protein selected from the group consisting of fructosyltransferase, levansucrase, alpha-amylase, invertase and starch branching enzyme and DNA encoding an antisense of stearyl-ACP desaturase.

A method of introducing one or more desired traits into hybrid rice designated HR170003 includes:

a) crossing a hybrid rice HR170003 plant, from which a representative sample of seed was deposited in the ATCC under the Budapest Treaty (Accession No. PTA-124255), with a plant of another rice cultivar that comprises a desired trait, to produce progeny plants, wherein the desired trait(s) is selected from the group consisting of male sterility, herbicide resistance, insect resistance, modified fatty acid metabolism, modified carbohydrate metabolism, and resistance to bacterial disease, fungal disease and viral disease;

b) selecting one or more progeny plants that have the desired trait(s) to produce selected progeny plants;

c) backcrossing the selected progeny plants with the HR170003 plants;

d) selecting for backcross progeny plants that have the desired trait(s); and e) repeating steps (c) and (d) three or more times to produce selected fourth or higher backcross progeny plants that comprise the desired trait(s).

A method of growing a blend of rice seed includes:

a) planting a blend comprising a first quantity of rice seed mixed with a second quantity of rice seed of another rice variety, rice hybrid or rice inbred;

b) growing the seeds to produce rice plants;

c) allowing cross pollination to occur between plants from first quantity of seed and plants from second quantity of seed; and d) harvesting seeds from the crossing the rice plants.

The blend may include seeds from a third, fourth or fifth rice variety, rice hybrid or rice inbred, and may include about 1% to about 95% of hybrid rice HR170003 seeds.

A method of producing a blend of rice seeds, includes:

a) providing a first quantity of rice seed;

b) providing a second quantity of rice seed of another rice variety, rice inbred or rice hybrid; and c) producing a blend comprised of mixing said first quantity of rice seed with said second quantity of rice seed.

The blend may include seeds from a third, fourth or fifth rice variety, and rice inbred, or rice hybrid and about 1% to about 95% of hybrid rice HR170003 seed.

DETAILED DESCRIPTION

Hybrid rice HR170003 is an intermediate-late maturing hybrid with a long grain, and low chalk values that was evaluated at multiple locations against a broad set of public varieties and potential hybrids for three years.

The hybrid disclosed herein has shown uniformity and stability as described in the following hybrid rice description information. It has been planted in a sufficient number of seasons with careful attention to uniformity of plant type. The hybrid has been produced with continued observation for uniformity.

A representative sample of the hybrid rice seed HR170003 was deposited with the ATCC (Accession No. PTA-124255) under the Budapest Treaty provision.

The following embodiments and aspects thereof are described in conjunction with systems, tools and methods which are meant to be exemplary and illustrative, not limiting in scope.

Within the scope of the claims are hybrid rice seeds, designated HR170003, the plants of hybrid rice HR170003, methods for producing a rice plant produced by crossing hybrid rice HR170003 with itself or another rice line or hybrid, and seeds and plants derived from the hybrid. "Derived" includes any plant part that traces its genetic origin to the deposited seeds including hybrid plants, seeds, and any further progeny or descendants of the hybrid derived by crossing hybrid rice HR170003 with other plants as a pollen donor or as a pollen recipient. Thus, any methods using hybrid rice HR170003 in backcrosses, hybrid production, crosses to develop populations, and the like, are within the scope of the present disclosure. All plants which are a progeny of or descend from hybrid rice HR170003 are within the scope of this disclosure. Hybrid rice HR170003 may be used in crosses with other, different, rice plants to produce first generation (F1) rice hybrid seeds and plants with different, possibly superior characteristics.

Single gene or multiple gene converted plants of hybrid rice HR170003 are disclosed. The single or multiple transferred gene(s) may preferably be a dominant or recessive allele. The single or multiple transferred gene(s) will confer such traits as herbicide resistance, insect resistance, resistance to bacterial, fungal, or viral diseases, male fertility, male sterility, enhanced nutritional quality, and/or industrial usage. The single or multiple gene(s) may be a naturally occurring rice gene, may be a gene modified as the result of artificial mutation of a naturally occurring gene, or a transgene introduced through genetic engineering techniques.

Regenerable cells are provided for use in tissue culture of hybrid rice HR170003. The tissue culture will preferably be capable of regenerating plants having the physiological and morphological characteristics of the foregoing rice plant, and of regenerating plants having substantially the same genotype as the foregoing rice plant. Genetic variants of hybrid rice HR170003 may be naturally generated through using tissue culture, or artificially induced utilizing mutagenic agents, or genome editing techniques during tissue culture. Suitable regenerable cells in such tissue cultures include embryos, protoplasts, meristematic cells, callus, pollen, cotyledon, leaves, flowers, anthers, roots, pistils, root tips, glumes, seeds, panicles or stems.

A blend consisting of rice seed of hybrid rice HR170003 with rice seed of a different inbred, rice variety, or rice hybrid is produced. Plants are grown from said seed and cross pollination occurs between the different plants produced from the seeds incorporated into the blend. The blend may also include a first quantity of seed of hybrid rice HR170003 with one, two, three, four, five or more quantities of rice seed of another rice hybrid, rice inbred or rice variety.

A blend of seed of hybrid rice HR170003 with seed of one, two, three, four, five or more of a different rice hybrid, rice variety or rice inbred is provided where hybrid rice HR170003 is present in proportions from 1% up to 95% of the blend, is disclosed. Methods for planting the blend produced with seeds of hybrid rice HR170003 and seeds of one, two three, four, five or more of another rice hybrid, rice variety or rice inbred and obtaining a crop with a mix of plants with hybrid rice HR170003 as a component. Further, harvest of seeds from a planted blend is for plants of which hybrid rice HR170003 is a component of the blend, for the purpose of utilizing such seeds for food; feed, as a raw material in industry, or as a seed source for planting.

In addition to the exemplary aspects and embodiments described previously, further aspects and embodiments will become apparent by study of the following descriptions.

TABLE 1

HYBRID RICE HR170003 DESCRIPTION
Hybrid rice HR170003 has the following morphologic and other characteristics, based primarily on data collected in Alvin, TX.[1]

Maturity

Days to Flowering: 85 days from emergence to 50% flowering
Maturity Class: Intermediate Late, (between 84 and 87 days)
Plant Height at Maturity Height: 122 cm
Height Class: Tall (greater than 115 cm)
Culm Angle (Degrees from perpendicular after flowering): Semi-erect
Internode Color (after flowering): Green
Strength (lodging resistance at maturity): Very strong
Flag Leaf (After Heading)

Length: 33.7 cm
Width: 1.6 cm
Pubescence: Intermediate
Leaf Angle: Erect
Blade Color: Green
Basal Leaf Sheath Color: Green
Ligule Length: 10.4 mm
Color (late vegetative state): Yellow-green
Shape: Cleft, tip is split
Collar Color (late vegetative stage): Green
Auricle Color (late vegetative stage): Yellow-green
Panicle Length: 28.5 cm
Type: Compact
Secondary Branching: Light
Exertion (near maturity): Moderately well exerted (panicle base is above the collar of the flag leaf blade)
Axis: Droopy
Shattering: Very low, (<1%)
Threshability: Easy (>50% of grains removed)
Grain (Spikelet)

Awns (after full heading): Absent
Apiculus Color (at maturity): Straw
Stigma Color: White
Stigma exertion (at flowering): 100% exertion, stigma fully outside glume
Lemma and Palea Color (at maturity): Straw
Lemma and Palea Pubescence: Short hairs
Spikelet Sterility (at maturity): Highly fertile, >90%
Grain (Seed)

Seed Coat Color: Light brown
Endosperm Type: Non-glutinous (non-waxy)
Endosperm Translucency: Clear
Endosperm Chalkiness: Small (less than 10% of sample)

TABLE 1-continued

HYBRID RICE HR170003 DESCRIPTION
Hybrid rice HR170003 has the following morphologic and other characteristics, based primarily on data collected in Alvin, TX.[1]

Scent: Non-scented
Shape Class (length/width ratio): Long
Milled Grain Measurements:

Length: 7.1 mm
Width: 2.1 mm
L/W Ratio: 3.4
Weight (1000 grains): 20 g
Milling Yield (% whole kernel -head rice to rough rice): 65%
Apparent Amylose: 27%
Alkali Spreading Value: 6.0 (2.3% KOH Solution)
Gelatinization Temperature Type: Low

[1]Information was collected in Alvin, Texas, at a fertilization rate of 168 kg/ha N.

In the following tables, probability figures indicate the probability associated with a paired Student's T-Test used to determine whether two samples are likely to have come from the same two underlying populations that have the same mean. The N.S. notation means that there is no significant difference between the means of the two samples.

Hybrid rice HR170003 is a widely-adapted hybrid that can be grown in the United States (US) and South America. In Tables 2 and 3, data was collected in the US and hybrid rice HR170003, is compared to Cheniere, a commonly grown cultivar in the US. In Tables 4 and 5, data was collected in South America and hybrid rice HR170003, is compared to IRGA 424, a commonly grown cultivar in South America.

Description of Varieties Used for Comparison

Cheniere: an early, high yielding, high quality semi-dwarf long-grain. It has displayed excellent yield potential, good lodging resistance and moderate resistance to physiological straight head. It is susceptible to blast and sheath blight. The variety has displayed excellent grain quality characteristics and is similar in maturity to Cypress. Saichuk, John et al., 2014 *Rice Varieties and Management Tips*. N.p.: LSU, 2014 (U.S. Pat. No. 7,141,725, PTA-5613).

IRGA 424: an intermediate maturing, high yielding, high tillering capacity, cold tolerant, long-grain that is popular in South America. This cultivar shows high response to fertilizers and topdressing making it a good option for high productivity. Martinez, C. P., et al., "Rice Breeding in Latin America", in Plant Breeding Reviews Vol. 38, Janick, et al., (Eds. pp. 240-241, Wiley-Blackwell, 2014).

Table 2, column 2 shows the yield in kilograms per hectare, column 3 shows the height in centimeters, column 4 shows the days to 50% flowering, column 5 shows the lodging score, column 6 gives the total milling percent, and column 7 shows the whole milling percent. The number of observations over which the data was collected is shown in row 4.

Table 2, hybrid rice HR170003 shows to be different from the US cultivar Cheniere. The hybrid rice HR170003, unexpectedly, has significantly greater grain yield, plant height, days to 50% flowering and lodging than the US cultivar, Cheniere. Yet, Cheniere has a greater total and whole milling percentages than hybrid rice HR170003. Data was collected during two years over a number of locations in the US.

TABLE 2

| 1 | 1 | 2 Yield (kg/ha) | 3 Plant Height (cm) | 4 Days to 50% Flowering | 5 Lodging Score | 6 Total Milling % | 7 Whole Milling % |
|---|---|---|---|---|---|---|---|
| 2 | HR170003 | 11,313 | 120 | 92 | 12 | 70 | 55 |
| 3 | Cheniere | 8,962 | 98 | 89 | 2 | 73 | 64 |
| 4 | Observations (n) | 35 | 23 | 32 | 35 | 34 | 34 |
| 5 | Difference | 2,351 | 22 | 3 | 10 | −3 | −9 |
| 6 | Probability | 0.000 | 0.000 | 0.000 | 0.002 | 0.000 | 0.000 |

In Table 3, column 2 shows the amylose percent, column 3 shows alkali spreading value (ASV), column 4 shows the milled grain length in millimeters (Length), column 5 shows the milled grain width in millimeters (Width), column 6 shows the milled grain length to width ratio (L/W Ratio), and column 7 shows the milled grain chalk percent. The number of observations over which the data was collected is shown in row 4.

As shown in Table 3, the quality characteristics of the grain harvested from hybrid rice HR170003 are different from those of cultivar Cheniere. Unexpectedly, hybrid rice HR170003 has a significantly higher ASV, milled grain length, width, and length to width ratio when compared to cultivar Cheniere. Both hybrid rice HR170003 and Cheniere have similar amylose and chalk values. Data was collected during two years over a number of locations in the US.

TABLE 3

| 1 | 1 | 2 Amylose % | 3 ASV | 4 Length (mm) | 5 Width (mm) | 6 L/W Ratio | 7 Chalk % |
|---|---|---|---|---|---|---|---|
| 2 | HR170003 | 26 | 7 | 7.0 | 2.1 | 3.4 | 2 |
| 3 | Cheniere | 26 | 5 | 6.7 | 2.0 | 3.3 | 2 |
| 4 | Observations (n) | 34 | 34 | 34 | 34 | 34 | 34 |
| 5 | Difference | 0 | 2 | 0.3 | 0.1 | 0.1 | 0 |
| 6 | Probability | N.S. | 0.000 | 0.000 | 0.000 | 0.000 | 0.066 |

In Table 4, column 2 shows the yield in kilograms per hectare, column 3 shows the height in centimeters, column 4 shows the days to 50% flowering, column 5 shows the lodging score, column 6 gives the total milling percent, and column 7 shows the whole milling percent. The number of observations over which the data was collected is shown in row 4.

As shown in Table 4, hybrid rice HR170003 unexpectedly has significantly greater grain yield, plant height, and total milling percentage than the variety IRGA 424. Yet, IRGA 424 has a significantly greater number of days to 50% flowering, whole milling percentage, and lodging score than hybrid rice HR170003. Data was collected during three years over a number of locations in South America.

TABLE 4

| 1 | 1 | 2 Yield (kg/ha) | 3 Plant Height (cm) | 4 Days to 50% Flowering | 5 Lodging Score | 6 Total Milling % | 7 Whole Milling % |
|---|---|---|---|---|---|---|---|
| 2 | HR170003 | 13,323 | 107 | 87 | 8 | 72 | 62 |
| 3 | IRGA 424 | 11,940 | 100 | 91 | 13 | 71 | 65 |
| 4 | Observations (n) | 75 | 18 | 58 | 27 | 64 | 64 |
| 5 | Difference | 1,383 | 7 | −4 | −5 | 1 | −3 |
| 6 | Probability | 0.000 | 0.000 | 0.000 | 0.014 | 0.001 | 0.000 |

In Table 5, column 2 shows the amylose percent, column 3 shows alkali spreading value (ASV), column 4 shows the milled grain length in millimeters (Length), column 5 shows the milled grain width in millimeters (Width), column 6 shows the milled grain length to width ratio (L/W Ratio), and column 7 shows the milled grain chalk percent. The number of observations over which the data was collected is shown in row 4.

As shown in Table 5, the quality characteristics of the grain harvested from hybrid rice HR170003 are different from those of cultivar IRGA 424. Hybrid rice HR170003, unexpectedly, shows a significantly higher amylose content, milled grain length, milled grain width, and chalk percentage when compared to cultivar IRGA 424. Nevertheless, IRGA 424 has a higher milled grain length to width ratio than hybrid rice HR170003. Both hybrid rice HR170003 and IRGA 424 have the same gelatinization temperature (ASV). Data was collected during three years over a number of locations in South America.

TABLE 5

| 1 | 1 | 2 Amylose % | 3 ASV | 4 Length (mm) | 5 Width (mm) | 6 L/W Ratio | 7 Chalk % |
|---|---|---|---|---|---|---|---|
| 2 | HR170003 | 26 | 7 | 6.8 | 2.1 | 3.3 | 4 |
| 3 | IRGA 424 | 25 | 7 | 6.6 | 2.0 | 3.4 | 3 |

TABLE 5-continued

| 1 | 1 | 2 Amylose % | 3 ASV | 4 Length (mm) | 5 Width (mm) | 6 L/W Ratio | 7 Chalk % |
|---|---|---|---|---|---|---|---|
| 4 | Observations (n) | 45 | 66 | 60 | 60 | 60 | 64 |
| 5 | Difference | 1 | 0 | 0.2 | 0.1 | −.1 | 1 |
| 6 | Probability | 0.000 | N.S. | 0.000 | 0.000 | 0.000 | 0.000 |

In Tables 6 and 7, starch characteristics of hybrid rice HR170003 are compared to Cheniere.

In Table 6, column 2 shows the peak viscosity expressed in Rapid Visco-Analyzer units (RVU), column 3 shows the peak time in minutes, column 4 shows the trough in RVU, column 5 shows the trough time in minutes, column 6 shows the paste temperature in degrees Celsius, and column 7 shows the paste time in minutes. In Table 7, column 2 shows the final viscosity in RVU, column 3 shows the breakdown in RVU, column 4 shows the setback in RVU, column 5 shows the consistency of the starch in RVU, column 6 shows the whiteness, and column 7 shows the transparency. The whiteness and transparency are expressed in light reflectance and transparency units, respectively, as measured by the Satake Milling Degree Meter.

As shown in Tables 6 and 7, hybrid rice HR170003 has a higher peak viscosity, peak time, trough, final viscosity, set back, consistency, and whiteness when compared to rice variety Cheniere. However, hybrid rice HR170003 has lower trough time, paste temperature, and breakdown when compared to rice variety Cheniere. Both hybrid rice HR170003 and Cheniere have the same paste time and transparency. Data presented in Tables 6 and 7 is from analysis made at the RiceTec, Inc. Grain Quality Lab with grain harvested in Alvin, Tex.

TABLE 6

| 1 | 1 | 2 Peak Viscosity (RVU) | 3 Peak Time (minutes) | 4 Trough (RVU) | 5 Trough Time (minutes) | 6 Paste Temperature (° C.) | 7 Paste Time (minutes) |
|---|---|---|---|---|---|---|---|
| 2 | HR170003 | 258.8 | 6.2 | 204.3 | 8.1 | 87.8 | 4.2 |
| 3 | Cheniere | 146.8 | 5.6 | 85.0 | 8.2 | 88.2 | 4.2 |
| 4 | Difference | 112 | 0.6 | 119.3 | −0.1 | −0.4 | 0 |

TABLE 7

| 1 | 1 | 2 Final Viscosity (RVU) | 3 Break Down (RVU) | 4 Set back (RVU) | 5 Consistency (RVU) | 6 Whiteness (light reflectance) | 7 Transparency |
|---|---|---|---|---|---|---|---|
| 2 | HR170003 | 376.1 | 54.8 | 117.3 | 171.8 | 48.2 | 3.5 |
| 3 | Cheniere | 199.3 | 61.8 | 52.5 | 114.3 | 46.8 | 3.5 |
| 4 | Difference | 176.8 | −7.0 | 64.8 | 57.5 | 1.4 | 0 |

Definitions

Unless otherwise defined, all technical and scientific terms herein have the same meaning as commonly understood by one of ordinary skill in the art to which this invention belongs. The terminologies that are used in the description of HR170003 herein is for the purpose of describing particular embodiments only and not intended to the limiting. All publications, patent applications, patent, and other references mentioned herein are incorporated by reference in their entirety. In the description and tables which follow, a number of terms are used. In order to provide a clear and consistent understanding of the specification and claims, including the scope to be given such terms, the following definitions are provided:

Alkali Spreading Value (ASV). A 1-7 index used as predictor of starch gelatinization temperature and established by the extent of disintegration of milled rice kernel in contact with a dilute alkali solution. Standard long grains have a 3 to 5 Alkali Spreading Value.

Allele. Allele is any one of many alternative forms of a gene, all of which relate to one trait or characteristic. In a diploid cell or organism, the two alleles of a given gene occupy corresponding loci on a pair of homologous chromosomes.

Alter. The utilization of up-regulation, down-regulation, or gene silencing.

Amylose. Type of grain starch that affects cooking behaviour. As such its measured quantity in rice is used to establish cooking properties of Standard US grain classes, or types (long, medium and short-grain).

Apiculus. Structures on the tip of the glume which are protrusions of the middle nerves of the bracts of the lemma and palea.

Apparent Amylose Percent. The percentage of the endosperm starch of milled rice that is amylose. Standard long grains contain 20 to 23 percent amylose. Rexmont-type long grains contain 24 to 25 percent amylose. Short and medium grains contain 14 to 16 percent amylose. Waxy rice contains zero percent amylose. Amylose values, like most characteristics of rice, will vary over environments. "Apparent" refers to the procedure for determining amylose, which may also involve measuring some long chain amylopectin molecules that bind to some of the amylose molecules. These amylopectin molecules actually act similar to amylose in determining the relative hard or soft cooking characteristics.

Auricle. Paired small appendages on either side of the base of the leaf blade.

Awns. An extension of the lemma apiculus.

Backcrossing. Process of crossing a hybrid progeny to one of the parents, for example, a first-generation hybrid F1 with one of the parental genotypes of the F1 hybrid.

Basal Leaf Sheath. Portion of the leaf that envelops the culm above the lowest node.

Breakdown. The Peak Viscosity minus the Trough Viscosity.

Cell. Cell as used herein includes a plant cell, whether isolated, in tissue culture or incorporated in a plant or plant part.

Chalk. An opaque region of the rice kernel resulting from loose packing of the starch granules. Chalk may occur throughout or in a part of the kernel.

Collar. Where the leaf sheath and leaf blade join

Consistency. The Final Viscosity minus the Trough Viscosity.

Cotyledon. A cotyledon is a type of seed leaf. The cotyledon contains the food storage tissues of the seed.

Culm. The rice plant's stem.

Cultivar. Cultivated variety, which is a genotype under cultivation.

Days to 50% flowering. Number of days from emergence to the day when 50% of all panicles are exerted at least partially through the leaf sheath. A measure of growth duration.

Embryo. The embryo is the small plant contained within a mature seed.

Endosperm. The largest part of the grain usually referred to as milled or white rice, having the seed coat (bran) and embryo (germ) removed.

Essentially all the physiological and morphological characteristics. A plant having essentially all the physiological and morphological characteristics of the hybrid or cultivar, except for the new characteristics derived from the converted gene.

Final Viscosity. The stickiness of rice flour/water slurry after being heated to 95° C. and uniformly cooled to 50° C. in a standardized instrument, specifically the Rapid Visco Analyzer. Viscosity at the end of the test also defined as Cool Paste Viscosity. (AACC Method 61-02)

Grain Length (L). Length of a whole rice grain measured in millimeters.

Gelatinization Temperature. The temperature at which the consistency of a rice flour-water mixture changes into a jelly. Correlates with the cooking time and texture of a rice product.

Gene Silencing. The interruption or suppression of the expression of a gene at the level of transcription or translation.

Genetically Modified. Describes an organism that has received genetic material from another, or had its genetic material modified, resulting in a change in one or more of its phenotypic characteristics. Methods used to modify, introduce or delete the genetic material may include mutation breeding, genome editing, backcross conversion, genetic transformation, single and multiple gene conversion, and/or direct gene transfer.

Genome Editing. A type of genetic engineering in which DNA is inserted, replaced, modified or removed from a genome using artificially engineered nucleases or other targeted changes using homologous recombination.

Genotype. Refers to the genetic constitution of a cell or organism.

Grain Width (W). Width of a whole rice grain measured in millimeters.

Grain Yield. Weight of grain harvested from a given area. Grain yield could also be determined indirectly by multiplying the number of panicles per area, by the number of grains per panicle, and by grain weight.

Harvest Moisture. The percent of moisture of the grain when harvested.

Hybrid. A plant that has been bred from two different parent plants.

Inbred Line. Seed and subsequent crops will have the same genetic makeup as the parent crop.

Internode. Area between nodes that is hollow with smooth outer surfaces and varying lengths.

Lemma and Palea. Together known as the glume, the larger five-nerved bract (lemma) that partly envelops the smaller three-nerved bract (palea), contain the floral organs.

Length/Width (L/W) Ratio. This ratio is determined by dividing the average length (L) by the average width (W).

Ligule. A membranous structure on the inner junction where the leaf sheath and the leaf blade meet that can vary in size, shape and color.

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A locus is a position, on a chromosome that confers one or more traits such as, for example, male sterility, herbicide resistance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Lodging Percent. Lodging is a subjective measured rating, and is the percentage of plant stems leaning or fallen completely to the ground before harvest.

Milled grain length. The length of the rice grain after the hull and pericarp are removed.

Milled grain width. The width of the rice grain after the hull and pericarp are removed.

Mixing. Physically mixing whole seeds of two or more genotypes of rice seed. For example, one of the genotypes of rice seed is hybrid rice HR170003 mixed with more than one, two, three, four, five or more genotypes of rice seed.

Multiple Gene Converted (Conversion). Multiple gene converted (conversion) includes plants developed by a plant breeding technique called backcrossing, wherein essentially all of the desired morphological and physiological characteristics of an inbred are recovered, while retaining two or more genes transferred into the inbred via crossing and backcrossing. The term can also refer to the introduction of multiple genes through genetic engineering techniques known in the art.

1000 Grain Weight. The weight of 1000 rice grains as measured in grams.

Paste Temperature. The temperature at which a defined flour-water mixture exhibits an initial viscosity increase under a standardized protocol utilizing the Rapid Visco Analyzer. Paste Temperature is an indication of gelatinization temperature.

Paste Time. The time at which Paste Temperature occurs.

Peak Temperature. The temperature at which Peak Viscosity is attained.

Peak Time. The time at which Peak Viscosity is attained.

Peak Viscosity. The maximum viscosity attained during heating when a standardized protocol utilizing the Rapid Visco Analyzer is applied to a defined rice flour-water slurry. (AACC Method 61-02).

Percent Identity. The extent to which two sequences have the same residues at the same positions in an alignment. Percent identity, as used herein, refers to the comparison of the homozygous alleles of two rice varieties. Percent identity is determined by comparing a statistically significant number of the homozygous alleles of two developed varieties. For example, a percent identity of 90% between rice variety 1 and rice variety 2 means that the two varieties have the same allele at 90% of their loci.

Percent Similarity. The extent to which nucleotide or protein sequences are related. Can be expressed as percent identity. Percent similarity, as used herein, refers to the comparison of the homozygous alleles of a rice variety with another rice plant, and if the homozygous allele of both rice plants matches at least one of the alleles from the other plant then they are scored as similar. Percent similarity is determined by comparing a statistically significant number of loci and recording the number of loci with similar alleles as a percentage. A percent similarity of 90% between the rice plant of this invention and another plant means that the rice plant matches at least one of the alleles of the other rice plant at 90% of the loci.

Plant. As used herein, the term "plant" includes reference to an immature or mature whole plant, including a plant from which seed or grain or anthers have been removed. Seed or embryo that will produce the plant is also considered to be the plant.

Plant Height. Plant height in centimeters is taken from soil surface to the tip of the extended panicle at harvest.

Plant Part. As used herein, the term "plant part" (or a rice plant, or a part thereof) includes protoplasts, leaves, stems, roots, root tips, anthers, seed, grain, embryo, pollen, ovules, cotyledon, hypocotyl, glumes, panicles, flower, shoot, tissue, cells, meristematic cells and the like.

Pubescence. This refers to a covering of very fine hairs closely arranged on the leaves, stems and glumes of the rice plant.

Quantitative Trait Loci (QTL). Genetic loci that controls to some degree numerically measurable traits that are usually continuously distributed.

Regeneration. Regeneration refers to the development of a plant from tissue culture.

Resistance/Resistant[2]. The inherited ability of a plant to survive and reproduce following exposure to a dose of herbicide normally lethal to the wild type; resistance may be naturally occurring or induced by such techniques as genetic engineering or selection of variants produced by tissue culture or mutagenesis.

[2]Weed Science Society of America, Weed Technology, vol. 12, issue 4 (October-December, 1998, p. 789)

RVA. Rapid Visco Analyzer is a widely used laboratory instrument utilized to examine the cooking properties of rice flour (i.e. paste time and thickening ability).

RVU. RAPID VISCO UNITS refer to the measurement units of the RVA.

Satake Milling Degree meter. A milling meter that simultaneously measures the degree of milling, comparative whiteness and degree of transparency of milled rice samples.

Semi-dwarf. A variety that is smaller than normal for its species.

Setback. The Final Viscosity minus Peak Viscosity.

Single Gene Converted (Conversion). Single gene converted (conversion) includes plants developed by a plant breeding technique called backcrossing wherein essentially all of the desired morphological and physiological characteristics of an inbred are recovered, while retaining a single gene transferred into the inbred via crossing and backcrossing. The term can also refer to the introduction of a single gene through genetic engineering techniques known in the art.

Tillering. New culms arising from buds in the axil.

Tolerance/Tolerant[1]. The inherent ability of a species to survive and reproduce after herbicide treatment implies that there was no selection or generic manipulation to make the plant tolerant. Resistance/tolerance are used somewhat interchangeably herein; for a specific rice plant genotype information is provided on the herbicide applied, the strength of the herbicide, and the response of the plant.

Total Milling (also called Milling Yield). The quantity of total milled rice produced in the milling of rough rice to a well-milled degree; it is usually expressed as a percent of rough rice by weight, but when specified, may be expressed as a percent of brown rice.

Transgene. A segment of DNA containing a gene sequence that has been isolated from one organism and is introduced into a different organism.

Transparency. The percentage of light transmitted through a milled grain of standard depth.

Trough Time. The time at which Trough Viscosity is attained.

Trough Viscosity. The minimum viscosity that occurs after Peak viscosity when a standardized protocol utilizing the Rapid Visco Analyzer is applied to a defined rice flour-water slurry. (AACC Method 61-02)

Variety. A group of plants having distinct uniform and stable traits which has been recommended for cultivation.

Whiteness. The percentage of light reflected from the milled grain sample.

Whole Milling (also called Head Rice Milling Yield). The quantity of milled head (¾ to whole kernels) rice produced in the milling of rough rice to a well-milled degree, usually expressed in the United States as a percent of rough rice by weight.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Materials and Methods

Methods for producing a rice plant include crossing a first parent rice plant with a second parent rice plant, wherein the first or second rice plant is a rice plant from hybrid rice HR170003. Further, both first and second parent rice plants may be from the hybrid rice HR170003. Therefore, other methods of using hybrid rice HR170003 include: selfing, backcrosses, hybrid breeding, and crosses to populations. Any plants produced using hybrid rice HR170003 as a parent is within the scope of this invention.

Methods for producing a hybrid rice HR170003-derived rice plant by crossing hybrid rice HR170003 with a second rice plant and growing the progeny seed, and repeating the crossing and growing steps with hybrid rice HR170003-derived plant from 0 to 7 times is disclosed. Any such methods using the hybrid rice HR170003 are disclosed, including: selfing, backcrosses, hybrid production, crosses to populations, and the like. All plants produced using hybrid rice HR170003 as a parent are within the scope of these claims, including plants derived from hybrid rice HR170003.

It should be understood that hybrid rice HR170003 can, through routine manipulation of cytoplasm or other factors, be produced in a male-sterile form. Such embodiments are also contemplated within the scope of the present claims.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils and the like.

Methods of Introducing New Trait or Locus into Hybrid Rice HR170003

Hybrid rice HR170003 represents a new base genetic hybrid into which a new locus, loci or trait(s) may be introgressed. Rice transformation, gene editing, backcross conversion with single or multiple genes, tissue culture method, double haploid techniques, pedigree breeding, mutation breeding and backcrossing are important methods that can be used to accomplish such an introgression.

A. Rice Transformation

The advent of new molecular biological techniques has allowed the isolation and characterization of genetic elements with specific functions such as encoding specific protein products. Scientists in the field of plant biology developed a strong interest in engineering the genome of plants to contain and express foreign genetic elements, or additional, or modified versions of native or endogenous in order to alter the traits of a plant in a specific manner. Any DNA sequences whether from a different species or from the same species which are inserted into the genome via transformation are referred to herein collectively as "transgenes". In some embodiments of the invention, a transgenic variant of hybrid rice HR170003 may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years, several methods for producing transgenic plants have been developed, and the present invention, in particular embodiments, also relates to transformed versions of the parents of the claimed hybrid.

A process for producing hybrid rice HR170003 with a desired trait, includes transforming hybrid rice HR170003 with a transgene that confers the desired trait. Another embodiment is the product produced by this process. The desired trait may be one or more of herbicide resistance, insect resistance, disease resistance, decreased phytate, or modified fatty acid or carbohydrate metabolism. The specific gene may be any known in the art or listed herein, including; a polynucleotide conferring resistance to imidazolinone, sulfonylurea, glyphosate, glufosinate, triazine, benzonitrile, cyclohexanedione, phenoxy proprionic acid, isoxazole, triketone and L-phosphinothricin; a polynucleotide encoding a *Bacillus thuringiensis* polypeptide, a polynucleotide encoding phytase, FAD-2, FAD-3, galactinol synthase or a raffinose synthetic enzyme.

Numerous methods for plant transformation have been developed, including biological and physical plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88.

1. *Agrobacterium*-mediated Transformation—One method of rice transformation is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

2. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., The Plant Journal 6:271-282 (1994) and U.S. Pat. No. 5,591,616 issued Jan. 7, 1997. Several methods of plant transformation collectively referred to as direct gene transfer have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., Bio/Technology 9:996 (1991). Additionally, liposome and spheroplast fusion have been used to introduce expression vectors into plants. Deshayes et al., EMBO J., 4:2731 (1985), Christou et al., Proc Natl. Acad. Sci. U.S.A. 84:3962 (1987). Direct uptakes of DNA into protoplasts using CaCl2 precipitation, polyvinyl alcohol or poly-L-ornithine have also been reported. Hain et al., Mol. Gen. Genet. 199:161 (1985) and Draper et al., Plant Cell Physiol. 23:451 (1982). Electroporation of protoplasts, whole cells, and tissues have also been described. Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994).

Following transformation of rice target tissues, expression of selectable marker genes that are described, allows for preferential selection of transformed cells, tissues and/or plants, using regeneration and selection methods now well known in the art.

B. Gene Editing Technique

In general, methods to modify, edit or alter plant endogenous genomic DNA include altering the plant native DNA sequence or a pre-existing sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Umov, et al., (2010) Nat Rev Genet. 11(9):636-46; Shukla, et al., (2009) Nature 459 (7245):437-41. A tran-scription activator-like (TAL) effector-DNA modifying enzyme (TALE or TALEN) is also used to engineer changes in plant genome. See e.g., US20110145940, Cermak et al. (2011), Nucleic Acids Res. 39(12) and Boch et al., (2009), Science 326(5959): 1509-12. Site-specific modification of plant genomes can also be performed using the bacterial type II CRISPR (clustered regularly interspaced short pal-indromic repeats)/Cas (CRISPR-associated) system. See e.g., Belhaj et al., (2013), Plant Methods 9: 39. The Cas9/guide RNA-based system allows targeted cleavage of genomic DNA guided by a customizable small noncoding RNA in plants (see e.g., WO 2015026883A1, incorporated herein by reference).

C. Backcross Conversions

A backcross conversion of hybrid rice HR170003 occurs when DNA sequences are introduced through backcrossing (Hallauer et al, 1988, "Corn Breeding" Corn and Corn Improvements, No. 18, pp. 463-481), with hybrid rice HR170003 utilized as the recurrent parent. Both naturally occurring and transgenic DNA sequences may be introduced through backcrossing techniques. A backcross conversion may produce a plant with a trait(s), locus or loci conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in Corn and Corn Improvement, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance and herbicide resistance. In addition, an introgression site itself, such as an FRT site, Lox site or other site-specific integration site, may be inserted by backcrossing and utilized for direct insertion of one or more genes of interest into a specific plant variety. In some embodiments of the invention, the number of loci that may be backcrossed into hybrid rice HR170003 is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of a site-specific integration system allows for the integration of multiple genes at the converted loci.

D. Tissue Culture and In-Vitro Regeneration of Rice Plants

Further reproduction of the hybrid can occur by tissue culture and regeneration. Tissue culture of various tissues of rice and regeneration of plants therefrom is well known and widely published. For example, reference may be had to Komatsuda, T. et al., Crop Sci. 31:333-337 (1991); Stephens, P. A., et al., Theor. Appl. Genet. (1991) 82:633-635; Komatsuda, T. et al., Plant Cell, Tissue and Organ Culture, 28:103-113 (1992); Dhir, S. et al., Plant Cell Reports (1992) 11:285-289; Pandey, P. et al., Japan J. Breed. 42:1-5 (1992); and Shetty, K., et al., Plant Science 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce rice plants having the physiological and morphological characteristics of hybrid rice HR170003.

As used herein, the term "tissue culture" indicates a composition comprising isolated cells of the same or a different type or a collection of such cells organized into parts of a plant. Exemplary types of tissue are protoplasts, calli, plant clumps, and plant cells that can generate tissue culture that are intact in plants or parts of plants, such as embryos, pollen, flowers, seeds, glumes, panicles, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, panicles, glumes, leaves, stems, pistils, anthers and the like. Thus, another aspect of this invention is to provide for cells which upon growth and differentiation produce a cultivar having essentially all of the physiological and morphological characteristics of hybrid rice HR170003. Genetic variants of hybrid rice HR170003 can also be obtained as a result of the tissue culture process. Variants recovered by tissue culture of hybrid rice HR170003 are within the scope of the disclosures.

A rice plant may be regenerated from a tissue culture of the hybrid rice plant disclosed herein. As is well known in the art, tissue culture of rice can be used for the in vitro regeneration of a rice plant. Tissue culture of various tissues of rice and regeneration of plants therefrom is well known and widely published. For example, reference may be had to Chu, Q. R., et al., (1999) "Use of bridging parents with high anther culturability to improve plant regeneration and breeding value in rice", Rice Biotechnology Quarterly 38:25-26; Chu, Q. R., et al., (1998), "A novel plant regeneration medium for rice anther culture of Southern U.S. crosses", Rice Biotechnology Quarterly 35:15-16; Chu, Q. R., et al., (1997), "A novel basal medium for embryogenic callus induction of Southern US crosses", Rice Biotechnology Quarterly 32:19-20; and Oono, K., "Broadening the Genetic Variability By Tissue Culture Methods", Jap. J. Breed. 33 (Suppl.2), 306-307, illus. 1983. Cells, which upon growth and differentiation, produce rice plants having the physiological and morphological characteristics of hybrid rice HR170003 are also within the scope of the disclosures.

Duncan, et al., Planta 165:322-332 (1985), reflects that 97% of the plants cultured that produced callus were capable of plant regeneration. Subsequent experiments with both cultivars and hybrids produced 91% regenerable callus that produced plants. In a further study in 1988, Songstad, et al., Plant Cell Reports 7:262-265 (1988), reports several media additions that enhance regenerability of callus of two cultivars. Other published reports also indicated that "non-traditional" tissues are capable of producing somatic embryogenesis and plant regeneration. K. P. Rao et al., Maize Genetics Cooperation Newsletter, 60:64-65 (1986), refers to somatic embryogenesis from glume callus cultures and B. V. Conger, et al., Plant Cell Reports, 6:345-347 (1987) indicates somatic embryogenesis from the tissue cultures of corn leaf segments. Thus, it is clear from the literature that the state of the art is such that these methods of obtaining plants are routinely used and have a very high rate of success.

E. Production of Double Haploids

The production of double haploids can also be used for the development of plants with a homozygous phenotype in the breeding program. For example, a rice plant for which hybrid rice HR170003 is a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989 and U.S. Pat. No. 7,135,615.

Methods for obtaining haploid plants are also disclosed in Kobayashi, M. et al., Journ. of Heredity 71(1):9-14, 1980; Pollacsek, M., Agronomie (Paris) 12(3):247-251, 1992; Cho-Un-Haing et al., Journ. of Plant Biol., 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Thomas, W J K, et al. (2003) "Doubled haploids in breeding" in Doubled Haploid Production in Crop Plants. Maluszynski, M., et al. (Eds.) Dordrecht, the Netherland Kluwer Academic Publishers. pp. 337-349.

F. Pedigree Breeding

Pedigree breeding starts with the crossing of two genotypes, such as hybrid rice HR170003 and another rice plant having one or more desirable characteristics that is lacking or which complements hybrid rice HR170003. Descriptions of breeding methods that are commonly used for different traits and crops can be found in one of several reference books (e.g., Allard, 1960; Simmonds, 1979; Sneep et al., 1979; Fehr, 1987). If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically, in the pedigree method of breeding, five or more successive filial generations of selfing and selection is practiced: F1 to F2; F2 to F3; F3 to F4; F4 to F5, etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a rice variety may be crossed with another rice variety to produce a first-generation progeny plant. The first-generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new rice varieties.

A method of making a backcross conversion of hybrid rice HR170003, includes the steps of crossing a plant of hybrid rice HR170003 with a donor plant having a desired trait, selecting an F1 progeny plant with the desired trait, and backcrossing the selected F1 progeny plant to a plant of hybrid rice HR170003 is within the scope of the disclosures. This method may further comprise the step of obtaining a molecular marker profile of hybrid rice HR170003 and using the molecular marker profile to select for a progeny plant with the desired trait and the molecular marker profile of hybrid rice HR170003. In one embodiment the desired trait is a mutant gene or transgene present in the donor parent.

G. Mutation Breeding

Mutation breeding is another method of introducing new traits into hybrid rice HR170003. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens such as base analogues, (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in "Principles of Cultivar Development" Fehr, 1993 Macmillan Publishing Company. In addition, mutations created in other rice plants may be used to produce a backcross conversion of hybrid rice HR170003 that comprises such mutation.

H. Breeding with Molecular Markers

Molecular markers may be used in plant breeding methods utilizing hybrid rice HR170003. Isozyme Electrophoresis and RFLPs have been widely used to determine genetic composition. See for example, Dinka, S. J., et al. (2007) "Predicting the size of the progeny mapping population required to positionally clone a gene" Genetics. 176(4): 2035-54; Gonzalez, C., et al. (2007) "Molecular and pathogenic characterization of new *Xanthomonas oryzae* strains from West Africa" Mol. Plant Microbe Interact. 20(5):534-546; Jin, H., et al. (2006) "Molecular and cytogenic characterization of an *Oryza officinalis—O. sativa* chromosome 4 addition hybrid and its progenies" Plant Mol. Biol. 62(4-5):769-777; Pan, G., et al. (2006) "Map-based cloning of a novel rice cytochrome P450 gene CYP81A6 that confers resistance to two different classes of herbicides" Plant Mol. Biol. 61(6):933-943.; Huang, W., et al. (2007) "RFLP analysis for mitochondrial genome of CMS-rice" Journal of Genetics and Genomics. 33(4):330-338; Yan, C. J., et al. (2007) "Identification and characterization of a major QTL responsible for erect panicle trait in *japonica* rice (*Oryza sativa* L.)" Theor. Appl. Genetics. DOI:10.1007/s00122-007-0635-9; and I. K. Vasil (ed.) DNA-based markers in plants. Kluwer Academic Press Dordrecht, the Netherlands.

SNP technology is currently the most efficient and practical marker technology; more marker loci can be routinely used. Gealy, David, et al. (2005) "Insights into the Parentage of Rice/red Rice Crosses Using SSR Analysis of US Rice Cultivars and Red Rice Populations". Rice Technical Working Group Meeting Proceedings. Abstract p. 179.; Lawson, Mark J., et al. (2006) "Distinct Patterns of SSR Distribution in the *Arabidopsis thaliana* and rice genomes" Genome Biology. 7:R14; Nagaraju, J., et al., (2002) "Genetic Analysis of Traditional and Evolved Basmati and Non-Basmati Rice Varieties by Using Fluorescence-based ISSR-PCR and SSR Markers" Proc. Nat. Acad. Sci. USA. 99(9):5836-5841; and Lu, Hong, et al. (2005) "Population Structure and Breeding Patterns of 145 US Rice Cultivars Based on SSR Marker Analysis" Crop Science. 45:66-76. Various molecular marker techniques may be used in combination to enhance overall resolution.

Rice DNA molecular marker linkage maps have been rapidly constructed and widely implemented in genetic studies such as in Zhu, J. H., et al. (1999) "Toward rice genome scanning by map-based AFLP fingerprinting" Mol. Gene Genetics. 261(1):184-195; Cheng, Z., et al (2001) "Toward a cytological characterization of the rice genome" Genome Research. 11(12):2133-2141; Ahn, S., et al. (1993) "Comparative linkage maps of the rice and maize genomes" Proc. Natl. Acad. Sci. USA. 90(17):7980-7984; and Kao, F. I., et al. (2006) "An integrated map of *Oryza sativa* L. chromosome 5" Theor. Appl. Genet. 112(5):891-902. Sequences and PCR conditions of SSR Loci in rice as well as the most current genetic map may be found in Rice-BLAST and the TIGR Rice Genome Annotation on the World Wide Web.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Genes, Locus/Loci, Agronomic Traits, Foreign Protein Genes that can be Used to Modify Hybrid Rice HR170003

Likewise, many agronomic genes as well as foreign protein genes can be transferred into hybrid rice HR170003 that will express a specific phenotype or have an altered genetic component. More particularly, plants can be genetically engineered to express various phenotypes of agronomic interest. Exemplary genes implicated in this regard include, but are not limited to, those in the following categories:

1. Genes that Confer Resistance to Disease and Insects

A. Plant disease resistance genes. Plant defenses are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* RSP2 gene for resistance to *Pseudomonas syringae*); McDowell & Woffenden, (2003) Trends Biotechnol. 21(4): 178-83 and Toyoda et al., (2002) Transgenic Res. 11 (6):567-82.

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., Plant Molec. Biol. 24:25 (1994), who disclose the nucleotide sequences of several *Clivia miniata* mannose-binding lectin genes.

D. A vitamin binding protein such as avidin. See PCT application US 93/06487. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* α-amylase inhibitor).

F. An insect specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7): 847-853; and Vasconcelos & Oliveira (2004) Toxicon 44 (4): 385-403. See also U.S. Pat. No. 5,266,317 to Tomalski et al., who disclose genes encoding insect-specific, paralytic neurotoxins.

H. Insect specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper-accumulation of a monoterpene, sesquiterpene, steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene, U.S. Pat. Nos. 7,145,060, 7,087,810 and 6,563,020.

K. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

L. A hydrophobic moment peptide. See PCT application WO 95/16776 and U.S. Pat. No. 5,580,852 which discloses peptide derivatives of Tachyplesin which inhibit fungal plant pathogens and PCT application WO 95/18855 and U.S. Pat. No. 5,607,914 which teaches synthetic antimicrobial peptides that confer disease resistance, the respective contents of which are hereby incorporated by reference.

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Intl Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

R. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

S. Genes involved in the Systemic Acquired Resistance (SAR) Response and/or the pathogenesis-related genes. Briggs, S., Current Biology, 5(2) (1995); Pieterse & Van Loon (2004) Curr. Opin. Plant Bio. 7(4):456-64 and Somssich (2003) Cell 113(7):815-6.

T. Antifungal genes. See Cornelissen and Melchers, Plant Physiol., 101:709-712 (1993); Parijs et al., Planta 183:258-264 (1991) and Bushnell et al., Can. J. of Plant Path. 20(2):137-149 (1998). Also see U.S. Pat. No. 6,875,907.

U. Detoxification genes, such as for fumonisin, beauvericin, moniliformin and zearalenone and their structurally related derivatives. For example, see U.S. Pat. No. 5,792,931.

V. Cystatin and cysteine proteinase inhibitors. See U.S. Pat. No. 7,205,453.

W. Defensive genes. See WO 03/000863 and U.S. Pat. No. 6,911,577.

2. Genes that Confer Resistance to a Herbicide, for Example:

A. A herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Mild et al., Theor. Appl. Genet. 80:449 (1990), respectively.

B. Glyphosate resistance conferred by mutant 5-enolpyruvlshikimate-3-phosphate synthase (EPSP) and aroA genes, respectively and other phosphono compounds such as glufosinate (phosphinothricin acetyl transferase (PAT) and *Streptomyces hygroscopicus* PAT bar genes), and pyridinoxy or phenoxy propionic acids and cyclohexanediones (ACCase inhibitor-encoding genes). See, for example, U.S. Pat. No. 4,940,835 to Shah, et al., which discloses the nucleotide sequence of a form of EPSP which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. No. 7,462,481. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European Application No. 0 242 246 to Leemans et al. DeGreef et al., Bio/Technology 7:61 (1989), describe the production of transgenic plants that express chimeric bar genes coding for PAT activity. Exemplary genes conferring resistance to phenoxy propionic acids and cyclohexanedione, such as sethoxydim and haloxyfop are the Acc1-S1, Acc1-S2 and Acc1-S3 genes described by Marshall et al., Theor. Appl. Genet. 83:435 (1992).

C. A herbicide that inhibits photosynthesis, such as a triazine (psbA and gs+ genes) or a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

B. Decreased phytate content, 1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene; 2) Up-regulation of a gene that reduces phytate content. In maize, this, for example, could be accomplished by cloning and then reintroducing DNA associated with one or more of the alleles, such as the LPA alleles identified in maize mutants characterized by low levels of phytic acid. See Raboy et al., Maydica 35:383 (1990) and/or by altering inositol kinase activity as in international publication numbers WO 02/059324, WO 03/027243, WO 99/05298, WO 2002/059324, WO 98/45448, WO 99/55882, WO 01/04147; U.S. Publication Numbers 2003/0009011, 2003/0079247; and U.S. Pat. Nos. 6,197,561, 6,291,224, 6,391,348.

C. Modified carbohydrate composition affected, for example, by transforming plants with a gene coding for an enzyme that alters the branching pattern of starch or a gene altering thioredoxin such as NTR and/or TRX (See U.S. Pat. No. 6,531,648 which is incorporated by reference for this purpose) and/or a gamma zein knock out or mutant such as cs27 or TUSC27 or en27 (See U.S. Pat. No. 6,858,778 and U.S. Publication Nos. 2005/0160488 and 2005/0204418, which are incorporated by reference for this purpose). See Shiroza et al., J. Bacteol. 170:810 (1988) (nucleotide sequence of *Streptococcus mutanns* fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus licheniformis* α-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley α-amylase gene), and Fisher et al., Plant Physiol. 102:1045 (1993) (maize endosperm starch branching enzyme II), WO 99/10498 (improved digestibility and/or starch extraction through modification of UDP-D-xylose 4-epimerase, Fragile 1 and 2, Ref 1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Altering conjugated linolenic or linoleic acid content, such as in international publication number WO 01/12800. Altering LEC1, AGP, Dek1, Superal1, mi1ps, various Ipa genes such as Ipa1, Ipa3, hpt or hggt. For example, see international publication numbers WO 02/42424, WO 98/22604, WO 03/011015, WO 02/057439, WO 03/011015; U.S. Pat. Nos. 6,423,886, 6,197,561, 6,825,397, 7,157,621; U.S. Publication No. 2003/0079247 and Rivera-Madrid, R. et al. Proc. Natl. Acad. Sci. 92:5620-5624 (1995).

E. Altered antioxidant content or composition, such as alteration of tocopherol or tocotrienols. For example, see U.S. Pat. Nos. 6,787,683 and 7,154,029 and international publication number WO 00/68393 involving the manipulation of antioxidant levels through alteration of a phytl prenyl transferase (ppt) and international publication number WO 03/082899 through alteration of a homogentisate geranyl geranyl transferase (hggt).

F. Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), international publication number WO 99/40209 (alteration of amino acid compositions in seeds), international publication number WO 99/29882 (methods for altering amino acid content of proteins), U.S. Pat. No. 5,850,016 (alteration of amino acid compositions in seeds), international publication number WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulphur), U.S. Pat. No. 5,912,414 (increased methionine), international publication number WO 98/56935 (plant amino acid biosynthetic enzymes), international publication number WO 98/45458 (engineered seed protein having higher percentage of essential amino acids), international publication number WO 98/42831 (increased lysine), U.S. Pat. No. 5,633,436 (increasing sulphur amino acid content), U.S. Pat. No. 5,559,223 (synthetic storage proteins with defined structure containing programmable levels of essential amino acids for improvement of the nutritional value of plants), international publication number WO 96/01905 (increased threonine), international publication number WO 95/15392 (increased lysine), U.S. Pat. Nos. 6,930,225, 7,179,955, 6,803,498, U.S. Publication No. 2004/0068767, international publication numbers WO 01/79516 and WO 00/09706 (Ces A: cellulose synthase), U.S. Pat. No. 6,194,638 (hemicellulose), U.S. Pat. Nos. 6,399,859 and 7,098,381 (UDPGdH) and U.S. Pat. No. 6,194,638 (RGP).

4. Genes that Control Male Sterility

Male sterility genes can increase the efficiency with which hybrids are made, in that they eliminate the need to physically emasculate the rice plant used as a female in a given cross. When one desires to employ male-sterility systems with a rice plant in accordance with the invention, it may be beneficial to also utilize one or more male-fertility restorer genes. For example, when cytoplasmic male sterility (CMS) is used, hybrid seed production requires three inbred lines: (1) a cytoplasmic male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent. The presence of a male-fertility restorer gene results in the production of fully fertile F1 hybrid progeny. If no restorer gene is present in the male parent, male-sterile hybrids are obtained. Such hybrids are useful when the vegetative tissue of the rice plant is utilized, but in most cases, the seeds will be deemed the most valuable portion of the crop, so fertility of the hybrids in these crops must be restored. Therefore, hybrid rice plant HR170003 comprising a genetic locus capable of restoring male fertility in an otherwise male-sterile plant is within the scope of the disclosures.

There are several methods of conferring genetic male sterility available, such as multiple mutant genes at separate locations within the genome that confer male sterility, as disclosed in U.S. Pat. Nos. 4,654,465 and 4,727,219 to Brar et al., and chromosomal translocations as described by Patterson in U.S. Pat. Nos. 3,861,709 and 3,710,511. In addition to these methods, Albertsen et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that, confers male fertility to be transcribed.

A. A tapetum-specific gene, RTS, a rice anther-specific gene, is required for male fertility and its promoter sequence directs tissue-specific gene expression in different plant species. Luo, Hong, et. al. (2006) Plant Molecular Biology. 62(3): 397-408(12). Introduction of a deacetylase gene under the control of a tapetum-specific promoter and with the application of the chemical N-Ac-PPT. See international publication number WO 01/29237.

B. Introduction of various stamen-specific promoters. Rice anther-specific promoters which are of particular utility in the production of transgenic male-sterile monocots and plants for restoring their fertility. See U.S. Pat. No. 5,639,948. See also international publications WO 92/13956 and WO 92/13957.

C. Introduction of the barnase and the barstar genes. See Paul et al., (1992) Plant Mol. Biol. 19:611-622.

For additional examples of nuclear male and female sterility systems and genes, see also, U.S. Pat. Nos. 5,859,341, 6,297,426, 5,478,369, 5,824,524, 5,850,014 and 6,265,640. See also Hanson, Maureen R., et al., (2004) "Interactions of Mitochondrial and Nuclear Genes That Affect Male Gametophyte Development" Plant Cell. 16: S154-S169, all of which are hereby incorporated by reference.

5. Genes that Affect Abiotic Stress Resistance

Genes that affect abiotic stress resistance (including but not limited to flowering, panicle/glume and seed development, enhancement of nitrogen utilization efficiency, altered nitrogen responsiveness, drought resistance or tolerance, cold resistance or tolerance, and salt resistance or tolerance) and increased yield under stress. For example, see: Xiong, Lizhong, et al., (2003) "Disease Resistance and Abiotic Stress Tolerance in Rice Are Inversely Modulated by an Abscisic Acid-Inducible Mitogen-Activated Protein Kinase" The Plant Cell. 15:745-759, where OsMAPK5 can positively regulate drought, salt, and cold tolerance and negatively modulate PR gene expression and broad-spectrum disease resistance in rice; Chen, Fang, et. al., (2006) "The Rice 14-3-3 Gene Family and its Involvement in Responses to Biotic and Abiotic Stress" DNA Research 13(2):53-63, where at least four rice GF14 genes, GF14b, GF14c, GF14e and Gf14f, were differentially regulated by salinity, drought, wounding and abscisic acid; U.S. Publication No. 2004/0148654 and International Publication No. WO 01/36596 where abscisic acid is altered in plants resulting in improved plant phenotype such as increased yield and/or increased tolerance to abiotic stress; International Publication Nos. WO 2000/006341 and WO 04/090143, U.S. Publication No. 2004/0237147 and U.S. Pat. No. 6,992,237 where cytokinin expression is modified resulting in plants with increased stress tolerance, such as drought tolerance, and/or increased yield. Also, see International Publication Nos. WO 02/02776, WO 2003/052063, WO 01/64898, JP2002281975 and U.S. Pat. Nos. 6,084,153, 6,177,275 and 6,107,547 (enhancement of nitrogen utilization and altered nitrogen responsiveness). For ethylene alteration, see U.S. Publication Nos. 2004/0128719 and U.S 2003/0166197 and International Publication No. WO 2000/32761. For plant transcription factors or transcriptional regulators of abiotic stress, see e.g. U.S. Publication Nos. 2004/0098764 and 2004/0078852.

Other genes and transcription factors that affect plant growth and agronomic traits such as yield, flowering, plant growth and/or plant structure, can be introduced or introgressed into plants, see U.S. Pat. No. 6,573,430 (TFL), 6,713,663 (FT), 6,794,560, 6,307,126 (GAI) and International Publication Nos. WO 2004/076638 and WO 2004/031349 (transcription factors).

Genetic Complements

The development of hybrid rice involves three steps: (1) selecting plants from various germplasm pools; (2) selfing the selected plants for several generations to produce a series of inbred plants, which although different from each other, each breed true and are highly uniform; and (3) crossing the selected inbred plants with unrelated inbred plants to produce F1 hybrid progeny. During this inbreeding process in rice, the vigor of the plants may decrease; however, vigor is restored when two unrelated inbred plants are crossed to produce F1 hybrid progeny. An important consequence of the genetic homozygosity and homogeneity of an inbred plant is that the F1 hybrid progeny of any two inbred varieties are genetically and phenotypically uniform. Plant breeders choose these hybrid populations that display phenotypic uniformity. Once the inbred plants that produce superior hybrid progeny have been identified, the uniform traits of their hybrid progeny can be reproduced indefinitely as long as the homogeneity of the inbred parents is maintained. The development of inbred plants generally requires at least 5 to 7 generations of selfing. Inbred plants are then cross-bred in an attempt to develop improved F1 hybrids. Hybrids are then screened and evaluated for adaptability for commercially important traits.

A hybrid rice plant characterized by molecular and physiological data obtained from the representative sample of the hybrid rice HR170003 deposited with the American Type Culture Collection (ATCC), and a hybrid rice plant formed by the combination of the disclosed hybrid rice plant or plant cell with another rice plant or cell, are within the scope of this disclosure.

In addition to phenotypic observations, a plant can also be identified by its genotype. The genotype of a plant can be characterized through a genetic marker profile which can identify plants of the same variety or a related variety or be used to determine or validate a pedigree. The present invention provides a genetic complement of the hybrid rice designated HR170003. As used herein, the phrase "genetic complement" means an aggregate of nucleotide sequences, the expression of which defines the phenotype of a rice plant or a cell or tissue of that plant. By way of example, a rice plant is genotyped to determine a representative sample of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest is also determined. The array of single locus genotypes is expressed as a profile of marker alleles, two at each locus. The marker allelic composition of each locus can be either homozygous or heterozygous. Homozygosity is a condition in which both alleles at a locus are characterized by the same nucleotide sequence or size of a repeated sequence. Heterozygosity refers to different conditions of the gene at a locus. A type of genetic marker for use with hybrid rice HR170003 is Single Nucleotide Polymorphism (SNPs), although potentially any other type of genetic marker could be used, for example, simple sequence repeat (SSRs), restriction fragment length polymorphisms (RFLPs), amplified fragment length polymorphisms (AFLPs), and isozymes. For example, see Cregan et. al, "An Integrated Genetic Linkage Map of the Soybean Genome" Crop Science 39:1464-1490 (1999), and Berry et al., Assessing Probability of Ancestry Using Simple Sequence Repeat Profiles: Applications to Maize Inbred Hybrids and Soybean Varieties" Genetics 165:331-342 (2003), each of which are incorporated by reference herein in their entirety.

Means of performing genetic marker profiles using SNP polymorphisms are well known in the art. In addition, plants and plant parts substantially benefiting from the use of hybrid rice HR170003 in their development, such as hybrid rice HR170003 comprising a backcross conversion, transgene, or genetic sterility factor, may be identified by having a molecular marker profile with a high percent identity to hybrid rice HR170003. Such a percent identity might be 95%, 96%, 97%, 98%, 99%, 99.5% or 99.9% identical to hybrid rice HR170003.

The marker profile of hybrid rice HR170003 also can be used to identify essentially derived varieties and other progeny varieties developed from the use of hybrid rice HR170003, as well as cells and other plant parts thereof. Such plants may be developed using the markers identified in international publication number WO 00/31964, U.S. Pat. Nos. 6,162,967 and 7,288,386. Progeny plants and plant parts produced using hybrid rice HR170003 may be identified by having a molecular marker profile with a genetic contribution from a rice hybrid or variety, as measured by either percent identity or percent similarity. Such progeny may be further characterized as being within a pedigree distance of hybrid rice HR170003, such as within 1, 2, 3, 4, or 5 or fewer cross-pollinations to a rice plant other than hybrid rice HR170003 or a plant that has hybrid rice HR170003 as a progenitor.

While determining the genetic marker profile of the plants described supra, several unique marker profiles may also be identified which did not appear in either parent of such rice plant. Such unique profiles may arise during the breeding process from recombination or mutation. A combination of several unique alleles provides a means of identifying a plant variety, an F1 progeny produced from such variety, and progeny produced from such rice plants.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

DEPOSIT INFORMATION

A deposit of the hybrid rice seed HR170003 designated Accession No. PTA-124255 that is owned by RiceTec, Inc., was made with the American Type Culture Collection (ATCC) 10801 University Boulevard, Manassas, Va. 20110 under the Budapest Treaty (37 CFR 1.801-1.809). The PTA certificates cited are only issued after viability is confirmed. The date of deposit was Jun. 20, 2017. Access to this deposit will be available during the pendency of this application to persons determined by the Commissioner of Patents and Trademarks to be entitled thereto under 37 CFR 1.14 and 35 USC 122. Upon allowance of any claims in this application, all restrictions on the availability to the public of the hybrid will be irrevocably removed by affording access to a deposit of at least 2,500 seeds of the same hybrid with the American Type Culture Collection, Manassas, Va.

The deposit will be maintained in the public repository for a period of 30 years or 5 years after the last request or for the effective life of the patent, whichever is longer. The deposit will be replaced if it should become inviable.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. Hybrid rice seed HR170003, wherein a representative sample of seed was deposited under ATCC Accession No. PTA-124255.

2. A rice plant, or a part thereof, produced by growing the seed of claim 1.

3. Pollen or an ovule of the plant of claim 2.

4. A tissue culture of cells produced from the plant of claim 2, wherein the cells of the tissue culture are produced from a plant part selected from the group consisting of leaves, pollen, embryos, cotyledon, hypocotyl, meristematic cells, roots, root tips, pistils, anthers, flowers, stems, glumes and panicles.

5. A protoplast produced from the plant of claim 2.

6. A protoplast produced from the tissue culture of claim 4.

7. A rice plant regenerated from the tissue culture of claim 4, wherein the plant has the morphological and all of physiological characteristics of hybrid rice HR170003, as listed in Table 1.

8. A method for producing a hybrid rice seed, wherein the method comprises crossing the plant of claim 2 with a rice plant with a different genetic complement and harvesting the resultant hybrid rice seed.

9. A method of producing a herbicide resistant rice plant, wherein the method comprises transforming the rice plant of claim 2 with a transgene, wherein the transgene confers tolerance to a herbicide selected from the group consisting of imidazolinone, cyclohexanedione, sulfonylurea, glyphosate, glufosinate, phenoxy proprionic acid, isoxazole, triketone, L-phosphinothricin, triazine and benzonitrile.

10. A method of producing an insect resistant rice plant, wherein the method comprises transforming the rice plant of claim 2 with a transgene that confers insect resistance.

11. A method of producing a rice plant with modified fatty acid metabolism or modified carbohydrate metabolism, wherein the method comprises transforming the rice plant of claim 2 with a transgene encoding a protein selected from the group consisting of fructosyltransferase, levansucrase, alpha-amylase, invertase and starch branching enzyme and DNA encoding an antisense of stearyl-ACP desaturase.

12. A method of introducing one or more desired traits into hybrid rice designated HR170003, wherein the method comprises:
 a) crossing a hybrid rice HR170003 plant, from which a representative sample of seed was deposited in the ATCC under the Budapest Treaty Accession No. PTA-124255, with a plant of another rice cultivar that comprises a desired trait or traits, to produce progeny plants, wherein the desired trait(s) are selected from the group consisting of male sterility, herbicide resistance, insect resistance, modified fatty acid metabolism, modified carbohydrate metabolism, and resistance to bacterial disease, fungal disease and viral disease;
 b) selecting one or more progeny plants that have the desired trait(s) to produce selected progeny plants;
 c) backcrossing the selected progeny plants with the HR170003 plants;
 d) selecting for backcross progeny plants that have the desired trait(s); and
 e) repeating steps (c) and (d) three or more times to produce selected fourth or higher backcross progeny plants that comprise the desired trait(s).

13. A plant produced by the method of claim 12, wherein the plant has the desired trait(s) and all of the physiological and morphological characteristics of hybrid rice HR170003 as listed in Table 1.

14. A method of growing a blend of rice seed, wherein the method comprises:
 a) planting a blend comprising a first quantity of rice seed of claim 1 mixed with a second quantity of rice seed of another rice variety, rice hybrid or rice inbred
 b) growing said seeds to produce rice plants;
 c) allowing cross pollination to occur between plants from first quantity of seed and plants from second quantity of seed; and
 d) harvesting seeds from the crossing of said rice plants.

15. The method of claim 14, wherein the blend further comprises seeds from a third, fourth or fifth rice variety, rice hybrid or rice inbred.

16. The method of claim 15, wherein the blend is comprised of about 1% to about 95% of hybrid rice HR170003 seed.

17. A method of producing a blend of rice seed, wherein the method comprises:
 a) providing a first quantity of rice seed of claim 1;
 b) providing a second quantity of rice seed of another rice variety, rice inbred or rice hybrid; and
 c) producing a blend comprised of mixing said first quantity of rice seed with said second quantity of rice seed.

18. The method of claim 17, wherein said blend is comprised of about 1% to about 95% of hybrid rice HR170003 seed.

* * * * *